(12) United States Patent
Pilloy et al.

(10) Patent No.: US 8,741,437 B2
(45) Date of Patent: *Jun. 3, 2014

(54) SUBSTRATE WITH ANTIMICROBIAL PROPERTIES

(71) Applicant: AGC Glass Europe, Louvain-la-Neuve (BE)

(72) Inventors: Georges Pilloy, Jumet (BE); Andre Hecq, Jumet (BE); Kadosa Hevesi, Jumet (BE); Nadia Jacobs, Jumet (BE)

(73) Assignee: AGC Glass Europe, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/949,561

(22) Filed: Jul. 24, 2013

(65) Prior Publication Data

US 2013/0309288 A1 Nov. 21, 2013

Related U.S. Application Data

(63) Continuation of application No. 11/721,691, filed as application No. PCT/EP2005/056884 on Dec. 16, 2005, now Pat. No. 8,530,056.

(30) Foreign Application Priority Data

Dec. 16, 2004 (EP) ..................... 04106648
Mar. 10, 2005 (EP) ..................... 05101882

(51) Int. Cl.
*B32B 15/04* (2006.01)
*B32B 17/06* (2006.01)

(52) U.S. Cl.
USPC ........... 428/432; 428/689; 428/697; 428/699; 428/701; 428/702

(58) Field of Classification Search
CPC ........ C03C 15/00; C03C 17/00; C03C 17/06; C03C 17/22; C03C 17/23; C03C 17/34; C03C 17/3411; C03C 17/3417; C03C 2217/70; C03C 2217/71; C03C 2218/00; C03C 2218/10; C03C 2218/15; C03C 2218/151; C03C 18/154; C03C 2218/156; C03C 2218/36; B32B 17/00; B32B 17/06; B32B 17/061; B32B 15/00; B32B 15/04; B32B 2250/04; B32B 2250/03; B32B 2255/00; B32B 2255/20; B32B 2255/205; B32B 2255/28; B32B 2264/00; B32B 2264/10; B32B 2264/105; B32B 2264/12; B32B 2307/70; B32B 2307/712; B32B 2307/754

USPC ......... 428/428, 432, 689, 697, 699, 701, 702; 204/192.1, 298.01, 298.02, 298.16
See application file for complete search history.

(56) References Cited

U.S. PATENT DOCUMENTS

| | | | |
|---|---|---|---|
| 5,595,813 A * | 1/1997 | Ogawa et al. | 428/212 |
| 6,677,063 B2 | 1/2004 | Finley | |
| 6,921,546 B2 | 7/2005 | Albach | |
| 7,211,323 B2 | 5/2007 | Erdemir et al. | |
| 7,323,249 B2 | 1/2008 | Athey et al. | |
| 7,527,832 B2 | 5/2009 | Sakoske et al. | |
| 7,862,910 B2 | 1/2011 | Krisko et al. | |
| 2002/0114945 A1 * | 8/2002 | Greenberg et al. | 428/336 |
| 2003/0235695 A1 | 12/2003 | Greenberg et al. | |
| 2005/0252108 A1 | 11/2005 | Sanderson et al. | |
| 2011/0081542 A1 | 4/2011 | Pilloy et al. | |

FOREIGN PATENT DOCUMENTS

| | | |
|---|---|---|
| JP | 06330285 | 11/1994 |
| JP | 11-322524 | 11/1999 |
| WO | 9513704 | 5/1995 |
| WO | WO2005/030665 | 4/2005 |

OTHER PUBLICATIONS

Ryu et al. ("Effect of calcination on the structural and optical properties of M/TiO2 thin films by RF magnetron co-sputtering", Materials Letters 58 (2004) 582-587).*

Ryu, et al., Effect of Calcination on the structural and optical properties of M/TiO2 thin films by RF magnetron co-sputtering, Feb. 2004, 58, p. 582-587.

* cited by examiner

*Primary Examiner* — David Sample
*Assistant Examiner* — Lauren Colgan
(74) *Attorney, Agent, or Firm* — Oblon, Spivak, McClelland, Maier & Neustadt, L.L.P.

(57) ABSTRACT

Substrate with Antimicrobial Properties An antimicrobial substrate (glass, ceramic or metallic) coated on at least one of its surface with at least one mixed layer deposited by a sputtering under vacuum magnetically enhanced process is described. The layer comprising at least one antimicrobial agent mixed to binder material chosen amongst the metal oxides, oxynitrides, oxycarbides or nitrides. This substrate present antimicrobial properties, in particular bactericidal activity even when no thermal treatment has been applied. If a tempered and antimicrobial glass is required, the same co-sputtering process can be used, optionally an underlayer can be added. Antimicrobial properties are maintained even after a tempering process.

19 Claims, No Drawings

SUBSTRATE WITH ANTIMICROBIAL PROPERTIES

This application is a continuation of U.S. Ser. No. 11/721,691 filed Jun. 14, 2007 (now U.S. Pat. No. 8,530,056), which is a 371 application of PCT/EP05/056884 filed Dec. 16, 2005. The contents of each of these applications are incorporated herewith by reference in their entirety.

The present invention relates to a substrate of any type: metal, glass, glass ceramic, wherein at least one of its surfaces has antimicrobial, in particular antibacterial or antifungal, properties. The present invention also relates to processes for the production of such a substrate.

In the field of ceramic substrates, EP 653 161, for example, describes the possibility of covering these with a glaze composed of silver to provide them with antibacterial properties.

In the field of glass-type substrates, sol-gel type processes are known to provide an antimicrobial surface. These processes require a hardening stage of the sol-gel layer, which involves elevated temperatures in the order of 500°-600° C. (sintering temperature). Processes are also known that require the substrate to be dipped in a composition comprising a silver salt. In this case, a silver layer is not deposited, but an ion exchange takes place in the solution at an elevated temperature.

A process for producing a glass substrate having antimicrobial properties is also known from EP 1449816. This process requires both a drying stage between 20° and 105° C. and a thermal treatment at 600°-650° C. This thermal treatment has some disadvantages particularly with respect to cost and uniformity of the product. Moreover, it renders the process very poorly reproducible, since it has been found that at these temperatures the diffusion of the silver is very rapid and a slight variation in the duration of the thermal treatment results in a significant variation in the depth of diffusion of the silver, and therefore this causes variation in the antibacterial properties of the substrate. It may also be noted that such a thermal treatment causes an undesirable yellow colouration of a soda-lime glass substrate. Furthermore, with this process, after having been treated, the product may no more be cut into particular size because of the necessary tempering process.

Therefore, there is a need to provide a substrate, either glass or metallic, with antimicrobial properties, which is easy to use and inexpensive to produce.

The present invention relates to a substrate coated with at least one mineral layer, particularly selected from metal oxides, oxynitrides, oxycarbides, carbides, DLC (diamond like carbon) or nitrides, said layer comprising at least one antimicrobial agent. In particular, the mineral layer can be selected from oxides of silicon, tin, zinc, titanium, niobium, aluminium, zirconium or mixture thereof, for example ZnSnOx. Particularly preferred nitrides are silicon, titanium and aluminium nitrides and mixture thereof.

The antimicrobial agent can be selected from various inorganic agents known for their antimicrobial properties, in particular silver, copper and zinc. Advantageously, the antimicrobial agent is in metallic form.

The substrate can be metallic, e.g. made of steel, or stainless steel or ceramic type or plastic or thermoplastic type substrate or a glass-type substrate, in particular a sheet of flat glass, particularly soda-lime glass which may be float glass. It may be clear glass or coloured glass. It may comprise a reflective layer (to form a mirror) or a layer of enamel or painting (for wall covering), generally at the surface opposite to the antimicrobial surface.

The substrate may have a thickness within the range of 2.5 to 12 mm.

The substrate may have a surface area of greater than 0.8 m to 0.8 m; it may be adapted to be cut to a finished size by a subsequent cutting operation.

In some embodiments of the invention, a substrate having antimicrobial agents present at at least one exposed surface may be an annealed sheet of glass. The term annealed sheet of glass is used herein to mean that the glass may be cut to size without breaking in the way that a tempered or hardened sheet of glass would break upon cutting. Such an annealed sheet of glass preferably has a surface compression of less than 5 MPa.

It has been found that it is possible to cause antimicrobial agents to diffuse into a mineral coating formed from one or more layers of metal oxides, oxynitrides, oxycarbides or nitrides, when this coating has been firstly deposited on a substrate of whatever type. The diffusion of the antimicrobial agent can also occur in a topcoat deposited above the layer containing the antimicrobial agent.

For example, the substrate can be coated with a first layer that blocks or slows down the diffusion of the antimicrobial agents and optionally with a second layer serving as a reservoir for the antimicrobial agents. Those functions can be ascertained on a product made according to the invention by comparing the antimicrobial effect of similar products with and without undercoating and/or by analysing diffusion profiles.

Each layers of the undercoat may in particular have a thickness comprised between 1 and 1000 nm, preferably between 1.5 and 800 nm, most preferably between 2 and 600 nm.

In particular, the blocking underlayer is chosen amongst pyrolitic and sputtered layers, in particular layers comprising metal oxide, metal or metal alloy compound, such as Pd, Ni—Cr, TiOx, NiCrOx, Nb, Ta, Al, Zr or ZnAl, or mixture thereof.

In the case of a glass substrate, it is conceivable that the antimicrobial glass substrate thus obtained is subjected to a thermal treatment stage such as thermal tempering, bending or hardening, while still retaining its antimicrobial properties.

In the case of metallic substrate, particularly preferred undercoat and/or mixed layers are chosen amongst titanium oxide, titanium nitride or zirconium oxide.

The substrate according to the invention preferably has an antibacterial effect on a large number of bacteria, whether gram positive or gram negative bacteria, in particular on at least one of the following bacteria: *Escherichia coli, Staphylococcus aureus, Pseudomonas aeruginosa, Enterococcus hirae*. The antibacterial effect measured in accordance with the standard JIS Z 2801 is in particular, at least on any one of these bacteria, higher than log 1, preferably higher than log 2 and particularly preferred higher than log 2.5. The substrate will be considered bactericidal according to the standard JIS Z 2810 if it has an effect higher than log 2. However, the invention also relates to substrates that have a lesser effect (for example bacteriostatic effect, which means that the bacteria are not necessarily killed but can not developed any more).

The substrate according to the invention advantageously has an antifungal (fungicidal or fungistatic) effect on at least one fungus, in particular *Candida albicans* or *Aspergillus niger*.

It has been found that it is possible to deposit the mineral layer and the antimicrobial agent in one single step over the entire substrate, whether it is made of metal, e.g. steel, or is a glass-type substrate. In particular, with the classic method of magnetron sputtering, it is possible to form a layer, e.g. of a metal oxide doped with an antimicrobial agent, e.g. silver, using two metal targets in the same deposition chamber (co-sputtering) or using a sole target with mixed metal. With this process no additional or subsequent diffusion of the antimicrobial agent may be needed. We obtain a antimicrobial substrate in one step, without any thermal treatment which is cost saving.

It has also been discovered that, if a tempered and antimicrobial glass is required, the same process may be used, and optionally an underlayer may be added. Antimicrobial (in particular bactericidal but also bacteriostatic) properties may be maintained even after a tempering process (implying high temperature treatment during perhaps 5 to 10 min).

Layers of Ag doped metal oxide deposited in a single step by co-sputtering, wherein the concentration of Ag can vary from 0.1 to 5%, have been made which have antimicrobial properties with a simple process which does not require any thermal treatment.

When the substrate used is a clear glass, it can advantageously have antimicrobial properties as well as a neutral colouration in reflection. In particular, the colorimetric indexes (CIELAB system) in reflection a* and b* (Illuminant C, 10° observer) may be in the range of between −10 and 6, preferably between −5 and 3 and particularly preferred between −2 and 0, and the purity may be less than 15%, preferably less than 10% and particularly preferred less than 5%.

If the substrate is a coloured glass, antimicrobial properties may be obtained without changing very much the initial colour of the substrate. The change of coloration is generally expressed with the colorimetric index by Delta E*; DeltaE*= $[(1^*_1-1^*_2)+(a^*_1-a^*_2)^2+(b^*_1-b^*_2)^2]^{1/2}$. A DeltaE* lower than 3, preferably lower than 2 may be obtained for an antimicrobial substrate according to the invention.

When the glass substrate used is a clear glass, it may advantageously have both antimicrobial properties and a visible light absorption of less than 1.5%, preferably less than 1.4% and particularly preferred less than 1.3%. It may have a visible light transmission within the range of 80 to 91%, preferably 84 to 90%. And the visible light reflection may be less than 15, preferably less than 12%, most preferably less than 10%.

The substrate according to the invention preferably has in particular an antimicrobial effect after at least one of the following accelerated ageing tests: wet spray test (test over 20 days in a chamber with a humidity of more than 95% at 40° C.), after 500 hours of UV irradiation (4 340A ATLAS lamps, chamber at 60° C.), after 24 hours immersed in a solution of $H_2SO_4$ (0.1 N), after 24 hours immersed in a solution of NaOH (0.1 N).

It may be advantageous to use an undercoat comprising an oxide of zirconium. This may particularly be so when the mixed layer comprises an antibacterial agent and an oxide of titanium, particularly comprising of consisting essentially of titanium oxide in its anatase crystallised form.

Additional or alternative embodiments of the present invention are described in dependant claims.

1. Substrate coated on at least one of its surface with at least one mixed layer deposited by a sputtering under vacuum (preferably magnetically enhanced) process, the layer comprising at least one antimicrobial agent mixed with a binder material chosen amongst metal oxides, oxynitrides, oxycarbides, carbides, DLC or nitrides, in particular $SiO_2$ $SnO_2$, $ZrO_2$, $ZnO$, $TiO_2$, $NbOx$, $Al_2O_3$, $Si_3N_4$, $TiN$, $AlN$ and mixture thereof.

2. Substrate according to embodiment 1, characterised in that it is coated with an underlayer with a function of slowing down or blocking the diffusion of antimicrobial agents.

3. Substrate according to embodiment 1 or 2, characterized in that the antimicrobial gent is selected from silver, copper and zinc.

4. Substrate according to any one of embodiments 1 to 3, characterized in that the total quantity of antimicrobial agents that it comprises is more than 0.1 $mg/m^2$, preferably more than 1 $mg/m^2$ and particularly preferred more than 10 $mg/m^2$ of antimicrobial surface.

5. Substrate according to any one of embodiments 1 to 4, characterized in that on at least one of the following bacteria: *E. coli, S. aureus, P. aeruginosa* (measured in accordance with the standard JIS Z 2801), it has a bactericidal effect higher than log 1, preferably higher than log 2 and particularly preferred higher than log 2.5.

6. Substrate according to any one of embodiments 1 to 5, characterized in that the layer comprises tin oxide and an antimicrobial agent selected from silver, copper and zinc.

7. Substrate according to any one of embodiments 1 to 6, characterized in that it is covered with an undercoating comprising a first layer based on $ZrO_2$ and a second layer based on $TiO_2$, in particular $TiO_2$ at least partially crystallised in the anatase form.

8. Substrate according to any one of embodiments 1 to 7, characterized in that the substrate is metallic.

9. Substrate according to any one of embodiments 1 to 6, characterized in that the substrate is a glass-type substrate.

10. Substrate according to embodiment 9, characterized in that it is able to be tempered at a later stage and in that it keeps antimicrobial properties after the treatment of tempering.

11. Substrate according to embodiment 9 or 10, characterized in that it presents annealed characteristics.

12. Process for the production of a substrate having antimicrobial properties, characterized in that it consists of depositing a mixed layer of a metal oxide doped with an antimicrobial agent by sputtering.

13. Process according to embodiment 12, characterized in that lwo separate targets are used.

14. Process according to embodiment 11 or 12, characterized in that the mixed layer consists of a layer of Ag doped $SiO_2$, $SnO_2$, $ZrO_2$, $ZnO$, $TiO_2$, $NbOx$, $Al_2O_3$, $Si_3N_4$, $TiN$, $AlN$ or mixture thereof, in particular $ZnSnOx$.

15. Process according to any one of embodiments 10 to 12, characterized in that a layer comprising from 2 to 1000 mg of antimicrobial agent per $m^2$ of substrate, preferably 10 to 250, most preferably 20 to 100 $mg/m^2$ is deposited on the substrate.

16. Process for the production of a tempered and antimicrobial glass type substrate comprising the steps of
depositing by sputtering vacuum process a mixed layer comprising an antimicrobial agent and a binder material;
(ii) tempering the coated substrate at temperature comprised between 600 and 800° C. during 5 to 15 min according to the thickness of the substrate.

17. Process according to embodiment 16, characterized in that at least one underlayer is deposited on the substrate before the deposition of step (i).

18. Process according to embodiment 17, characterized in that the underlayer has a function of blocking or slowing down the migration of the antimicrobial agent during the tempering step.

19. Process according to embodiment 17 or 18, characterized in that the underlayer is chosen amongst pyrolitic and sputtered layers, in particular layers comprising metal oxide, metal or metal alloy compound, such as Pd, Ni—Cr, TiOx, NiCrOx, Nb, Ta, Al, Zr or ZnAl, or mixture thereof.

The present invention shall be described in more detail below, in a non-restrictive manner:

EXAMPLE 1

Two samples of clear soda-lime glass were coated with a layer of $SiO_2(Al):Ag$ by co-sputtering. Two metal targets were used in a mixed atmosphere of argon and oxygen: one was composed of silicon doped with 8% Al and the second target was a metallic silver target. The electric power supply to the layers was regulated in order to obtain 0.5 atomic % of Ag in the layer for the first sample and 1 atomic % of Ag in the layer for the second. The layer thickness was 80 nm for the first sample and 150 nm for the second.

The bactericidal and fungicidal properties (in particular on *E. Coli*) of the samples were analysed in accordance with standard JIS Z 2801. A log 1 level indicates that 90% of the bacteria inoculated onto the surface of the glass were killed in 24 hours in the conditions of the standard; log 2 indicates that 99% of the bacteria were killed; log 3 indicates that 99.9% of the bacteria deposited were killed etc.

A value of log 4.2 was obtained for both samples of example 1.

EXAMPLE 2

Two samples of clear soda-lime glass were coated with a layer of $SnO_2$—Ag by co-sputtering using two metallic targets (Sn and Ag). The thickness of the layer is respectively 80 and 40 nm and the quantity of Ag deposited is respectively 2 and 30 mg/m2. The antibacterial effect was measured in the same manner as in the previous example. Values of log 4.4 and 4.5 were obtained.

EXAMPLE 3

Two samples of clear soda-lime glass were coated with a layer of ZrO2-Ag by co-sputtering using two metallic targets (Zr and Ag). The electric power supply to the layers was regulated in order to obtain 1.2 atomic % of Ag for the first sample and 3.4 atomic % of Ag for the second. The antibacterial effect was measured in the same manner as in the previous examples. Values of log 4 were obtained for both samples.

EXAMPLE 4

A co-sputtering of SnO2-Ag was deposited over two different substrates. The quantity of Ag deposited amounts to 46 mg/m2 of surface and the thickness of the mixed layer is 17 nm.

The first substrate is a clear soda lime glass with an double underlayer SiOx (70 nm) and SnO2:F (320 nm) deposited by Chemical Vapor Deposition. The second substrate is a clear soda lime-glass coated with a 50 nm thick SiO2 layer deposited by vacuum sputtering. Both samples were subjected to a common tempering process (670° C. during 10 min follow by quick cooling).

The antibacterial effect on *E. Coli*, measured as in the previous examples gives values of log 1.76 and 1.38. This meant a bactericid effect were between 90 and 99% of the inoculated bacteria were killed.

EXAMPLE 5

A co-sputtering of SnO2-Ag was deposited over 2 different metallic substrates. The quantity of Ag deposited amounts to 46 mg/m2 of surface and the thickness of the mixed layer is 17 nm.

The first substrate is a galvanized steel of the commercial type "ST37" with a thickness of 1.5 mm. The second substrate is a sample of steel laminated under cold condition and without oil of a thickness of 0.2 mm.

The antibacterial effect on *E. Coli*, measured as in the previous examples gives values of log 3.53 for both samples.

The invention claimed is:

1. A glass substrate, comprising:
   a glass substrate;
   an undercoating present on said glass substrate, said undercoating comprising a first layer of $ZrO_2$ and a second layer of $TiO_2$;
   a mixed layer coated on a least one surface of said glass substrate,
   to form a coated glass substrate, wherein
   said mixed layer comprises an antimicrobial agent to promote antimicrobial properties and at least one binder material selected from the group consisting of a metal oxide, an oxynitride, an oxycarbide, a carbide, a DLC, and a nitride, provided that titanium oxide and zirconium oxide are excluded from the mixed layer, and
   said antimicrobial agent comprises silver in a concentration of from 0.1 to 5%.

2. The glass substrate according to claim 1, wherein said mixed layer is deposited by sputtering under a vacuum process.

3. The glass substrate according to claim 1, wherein said mixed layer is deposited by sputtering under a magnetically enhanced vacuum process.

4. The glass substrate according to claim 1, wherein said at least one binder material is at least one material selected from the group consisting of $SiO_2$, $SnO_2$, ZnO, NbOx, $Al_2O_3$, $Si_3N_4$, TiN, and AlN.

5. The glass substrate according to claim 1, which presents annealed characteristics.

6. The glass substrate according to claim 1, wherein, on at least one of the following bacteria: *E. coli, S. aureus, P. aeruginosa* (measured in accordance with the standard JIS Z 2801), the antimicrobial agent has a bacterial effect higher than log 1.

7. The glass substrate according to claim 1, wherein, on at least one of the following bacteria: *E. coli, S. aureus, P. aeruginosa* (measured in accordance with the standard JIS Z 2801), the antimicrobial agent has a bacterial effect higher than log 2.

8. The glass substrate according to claim 1, wherein, on at least one of the following bacteria: *E. coli, S. aureus, P. aeruginosa* (measured in accordance with the standard JIS Z 2801), the antimicrobial agent has a bacterial effect higher than log 2.5.

9. The glass substrate according to claim 1, wherein said second layer of $TiO_2$ is in anatase form.

10. A glass substrate, comprising:
    a glass substrate;
    an undercoating present on said glass substrate, said undercoating comprising a first layer of $ZrO_2$ and a second layer of $TiO_2$;
    a mixed layer coated on a least one surface of said glass substrate,
    to form a coated glass substrate, wherein
    said mixed layer comprises an antimicrobial agent to promote antimicrobial properties and at least one binder material selected from the group consisting of $SnO_2$, NbOx, an oxynitride, an oxycarbide, a carbide, DLC, and a nitride, provided that titanium oxide and zirconium oxide are excluded from the mixed layer, and said antimicrobial agent is selected from the group consisting of silver and copper.

11. The glass substrate according to claim 10, wherein said mixed layer is deposited by sputtering under a vacuum process.

12. The glass substrate according to claim 10, wherein said mixed layer is deposited by sputtering under a magnetically enhanced vacuum process.

13. The glass substrate according to claim 10, wherein said mixed layer comprises the antimicrobial agent in an amount of from 2 to 1000 mg per $m^2$ of substrate surface.

14. The glass substrate according to claim 10, wherein said mixed layer comprises the antimicrobial agent in an amount of from 10 to 250 mg per $m^2$ of substrate surface.

15. The glass substrate according to claim 10, wherein said mixed layer comprises the antimicrobial agent in an amount of from 20 to 100 mg per $m^2$ of substrate surface.

16. The glass substrate according to claim 10, wherein said mixed layer comprises Ag doped $SnO_2$, $NbOx$, $Si_3N_4$, TiN, or AlN, or a mixture thereof.

17. The glass substrate according to claim 10, wherein said mixed layer comprises Ag doped ZnSnOx.

18. The glass substrate according to claim 10, which presents annealed characteristics.

19. The glass substrate according to claim 10, wherein said second layer of $TiO_2$ is in anatase form.

* * * * *